United States Patent [19]

Fleischman

[11] Patent Number: 5,225,859

[45] Date of Patent: Jul. 6, 1993

[54] APPARATUS AND METHOD FOR CAPTURE AND PROCESSING OF OCULAR AND RETINAL IMAGES

[75] Inventor: Jay A. Fleischman, Greenwich, Conn.

[73] Assignee: Hemozoin Scientific, Inc., Tucson, Ariz.

[21] Appl. No.: 775,689

[22] Filed: Oct. 10, 1991

[51] Int. Cl.⁵ .............................................. A61B 3/14
[52] U.S. Cl. .................................... 351/206; 351/221; 351/246
[58] Field of Search ................. 351/206, 205, 221, 246

[56] References Cited

U.S. PATENT DOCUMENTS 4,854,691  8/1989  Sekine et al. .................... 351/221

Primary Examiner—Rodney B. Bovernick
Assistant Examiner—Hung Xuan Dang
Attorney, Agent, or Firm—Rosenbaum & Schwartz

[57] ABSTRACT

A combined apparatus for the capture, processing and archival recording of digital or analog images of the ocular and retinal anatomy by indirect ophthalmoscopy and fluorescence angiography.

14 Claims, 2 Drawing Sheets

APPARATUS AND METHOD FOR CAPTURE AND PROCESSING OF OCULAR AND RETINAL IMAGES

BACKGROUND OF THE INVENTION

The present invention relates generally to fundus and ocular cameras and indirect ophthalmoscopes used by ophthalmologists or ophthalmic photographers to capture and record images of the ocular and retinal anatomy used in diagnosis of ocular and retinal abnormalities. More particularly, the present invention relates to a combined apparatus for the capture, processing and archival recording of digital or analog images of the ocular and retinal anatomy.

Generally there are three methods used to photographically document the retinal fundus with an eye fundus camera. The first method is to take a picture of the eye fundus using visible light, the second method is to take a picture of the eye fundus vasculature using a fluorescent dye, known as fluorescein angiography and the third method is to take a picture of the eye choroidal vasculature using and infrared light stimulated dye, known as indocyanine green angiography.

Fluorescein angiography is a widely used method in which a fluorescent dye, typically sodium fluorescein ($C_{20}H_{12}O_5Na$), and more recently indocyanine green, is administered intravascularly to the patient and the eye fundus is exposed to light energy to excite the fluorescein in the eye fundus vasculature. Excitation of the fluorescein causes a fluorescence which is visible to the practitioner when using certain optical filters and may be recorded by photography.

Fluorescence is luminescence which is maintained only by exposure to a continuous excitatory energy. Fluorescence is emission of light immediately after excitation and cessation of emission immediately after cessation of excitatory radiation. Luminescence refers generally to the emission of light due to any cause other than high temperature. The second law of thermodynamics dictates that emitted energy must be less than the energy absorbed. Thus, since energy and wavelength are reciprocally related, luminescence, and, hence, fluorescence, always entails a shift from a shorter wavelength, i.e., higher energy, in the excitation radiation to a longer wavelength, i.e., lower energy, in the emitted light.

Sodium fluorescein, for example, in solution at proper concentration and pH, is excited by light energy between 465 to 490 nm in the blue portion of the light spectrum, and fluoresces at a peak wavelength of 520 to 530 nm in the green-yellow portion of the light spectrum. As with all known fluorescent materials, sodium fluorescein has an energy absorption curve which decreases in the shorter wavelength and rapidly in the longer wavelengths, and a fluorescence which rises rapidly over the shorter wavelengths and diminishes slowly over the longer wavelengths. Sodium fluorescein is known to fluoresce over a spectral curve range of 485 to 600 nm.

Fluorescein angiography is typically conducted by intravenously injecting sodium fluorescein into an arm vein of the subject to be tested. The normal fluorescein angiogram can be divided generally into the following phases:
i. early choroidal filling and choroidal flush;
ii. retinal artery filling and increased choroidal filling;
iii. arterio-venous filling and laminar flow;
iv. full arterio-venous filling;
v. retinal venous phase; and
vi. late arterio-venous recirculation phase with decreased retinal and choroidal fluorescence.

It usually takes about 5 to 10 seconds before the fluorescein enters the eye fundus vasculature. The early signs of fluorescence is referred to as the "choroidal flush" due to entry of the fluorescein into the choroid. This choroidal fluorescence is seen because unbound fluorescein molecules pass through the fenestra of the choriocapillaris and fill the extracellular choroidal space. One to two seconds after the choroidal flush is noted, fluorescence appears in the central retinal artery and the larger precapillary arteriole branches. The fluorescein then passes into the retinal capillaries, the post capillary venules and the major retinal veins and the central retinal vein. The early phase of the retinal venous fluorescein pattern is often referred to as laminar flow. This laminar flow provides a characteristic picture because the vascular flow is faster in the center of the larger retinal veins than on the sides. The fluorescence along the walls of the veins becomes thicker, and eventually there is a complete fluorescence within the lumen of the vein. Fluorescence of the disc originates from the posterior ciliary vascular system and from the capillaries of the central retinal artery on the surface of the disc. The macular region of the normal fluorescein angiogram characteristically has a darker appearance than the surrounding region. Xanthophyll in the sensory retina partially blocks blue light transmission needed to excite the fluorescein in the choroid. Additionally, the increased density of the melanin pigment granules in the retinal pigment epithelium underlying the macula also block some of the choroidal fluorescence during fluorescein fundus angiography. In the case of indocyanine green fundus angiography, both the infrared excitation wavelength and infrared fluorescence wavelength easily pass through the xanthophyll and melanine pigment layers to reveal details of the choriodal vasculature layer.

During fluorescein angiography, a flash of white light from a retinal fundus camera passes through a blue excitation optical filter which passes blue light having a peak wavelength of 465 to 490 nm and strikes the fluorescein molecules in the ocular vasculature. The blue light excites the fluorescein molecules which fluoresce and emit a yellow green light with a peak wavelength of 520 to 530 nm. Both yellow-green light as well as reflected blue light emerges from the patient's eye. A yellow-green optical barrier filter is used to block the blue light and transmit only the yellow-green wavelengths onto camera film and to the viewing oculars.

As noted above, angiography of the eye fundus typically employs sodium fluorescein dye as the imaging medium. Information concerning the dynamics of retinal and choroidal circulation have been derived principally from fluorescein angiography. Except for the earliest choroidal arterial filling, i.e., the choroidal flush, visualization of the choroidal circulation is limited by both the spectral characteristics of the eye pigments and tissue and the rapid extravasation of fluorescein from the choriocapillaris.

As noted by Hochheimer, et al., U.S. Pat. No. 3,893,447, choroidal circulation may be visualized separately from the retinal circulation by using indocyanine green dye. The methods and principles concerning indocyanine green fundus angiography are essentially identical to fluorescein fundus angiography. The principal difference with fluorescein fundus angiography is that indocyanine green fluoresces in the infrared spectrum and allows visualization of the choroidal circulation dynamics on infrared film or by and infrared detector. As taught by Hochheimer, sodium fluorescein may be mixed with indocyanine green and the mixture injected intravenously. Angiograms of the separate circulation are simultaneously produced by two cameras mounted on a fundus camera equipped with an optical separation device. The light energy returning from the ocular fundus during each flash firing is split by the optical separator into two or more discrete beams. One split beam corresponds to the spectral range of the sodium fluorescein fluorescence, i.e., 490–520 nm, in the retinal circulation, while the second split beam corresponds to the absorption spectrum of indocyanine green, which is near 800 nm, in the choroidal circulation. In the infrared spectrum at about 800 nm, macular xanthophyll and the pigment epithelium are relatively transparent and energy absorption by indocyanine green is detectable. The two cameras are equipped with appropriate optical filters to pass only the yellow-green light of the sodium fluorescein or the infrared light of the indocyanine green dye.

Fluorescein angiography typically employs two optical filters; an exciter filter and a barrier filter. The exciter filter transmits blue light at 465 nm to 490 nm, the absorption peak of fluorescein excitation. The barrier filter transmits light at 525 to 530 nm, the fluorescent peak of fluorescein. Optimally, there should be little or no overlap between the filter curves to eliminate pseudofluorescence. Pseudofluorescence is non-fluorescent light which passes through both the exciter and barrier filters. Pseudofluorescent light records onto black and white film and results in reduced contrast and artefactual fluorescence. Conventional optical filters are available as matched sets from Baird-Atomic, Spectrotech and De Lori.

Imaging of the peripheral retina using standard fundus cameras is a difficult task which requires a high degree of skill and practice. Problems with patient position, alignment and focusing are compounded by marginal corneal astigmatism, unsteady patients, light reflexes and awkward camera displacement. While various cameras employ different compensating mechanisms, peripheral imaging remains a significant shortcoming of conventional fundus cameras.

Finally, current fundus cameras employ a variety of films to record the fluorescent light emanating from the retina. The film most frequently used in Kodak "TRI-X" film which is a fairly fast film of ASA 400. Angiographers also employ a variety of different film development techniques which enhance detail but compromise contrast. The developed negatives or prints made from the resulting negatives are often enclosed in patient record files. Videocameras may be employed in place of the film camera as illustrated by European Patent Application No. 153,570 published Jan. 16, 1985.

Indirect ophthalmoscopy is a method which permits visualization of the peripheral retinal area. Examples of indirect ophthalmoscopes and methods of ophthalmoscopy are provided by U.S. Pat. No. 4,146,310 to Kohayakawa, Y., et al., U.S. Pat. No. 4,018,514 to Plummer, and U.S. Pat. No. 3,881,812 to Ben-Tovim. Each of these systems employ a lamp, a mirror worn on a harness placed on the observer's head, and a lens which the observer must hold in front of the eye to be examined. Use of indirect ophthalmoscopes requires positioning of the light relative to the both the observer's and subject's eye, positioning the mirror at a proper angle and placing the lens at a defined distance from the subject's eye and tilted to exclude reflexes. The retina is observed through the lens held in front of the patient's eye. A film or video camera is sometimes used in conjuction with the indirect ophthalmoscope to photographically record the retinal image.

Current fundus cameras cost tens of thousands of dollars and add-on video cameras or image processing equipment only adds to the total system cost. Moreover, processing and manipulating the current film or video images requires cumbersome and expensive digitization as a separate process which further increases cost and introduces a time delay into the diagnostic process. With the advent of floppy disc based video and still cameras, direct analog and digital processing of the retinal images obtained by either a fundus camera or an indirect ophthalmoscope is possible. Moreover, the use of optical barrier filters requires careful matching to the exciter filter to minimize pseudofluorescence. There is, however, usually some remaining spectral overlap which tends to degrade image quality. Electronic imaging processing permits the elimination of the barrier filter by electronically filtering all wavelengths except that desired for imaging and recording purposes.

SUMMARY OF THE INVENTION

An indirect ophthalmoscopy/fundus camera is provided which incorporates full visible spectrum, partial spectrum, or infrared sensitive still or video cameras, an analog or digital recorder, a beam splitter to pass 800 nm wavelength signals to the infrared videocamera, in the case where indocyanine green dye fluorescence is to be recorded, electronic filters which process light emitting from the retina and passes only 520 nm wavelength yellow-green signals, and control processors for the purpose of color and fluorescent fundus imaging, including, for example fluorescein and indocyanine green fluorescent fundus imaging. The invention incorporates an automatic synchronization between an intravenous dye injector and the recorder operating sequences.

DETAILED DESCRIPTION OF THE PREFERRED EMBODIMENTS

Figure 1:
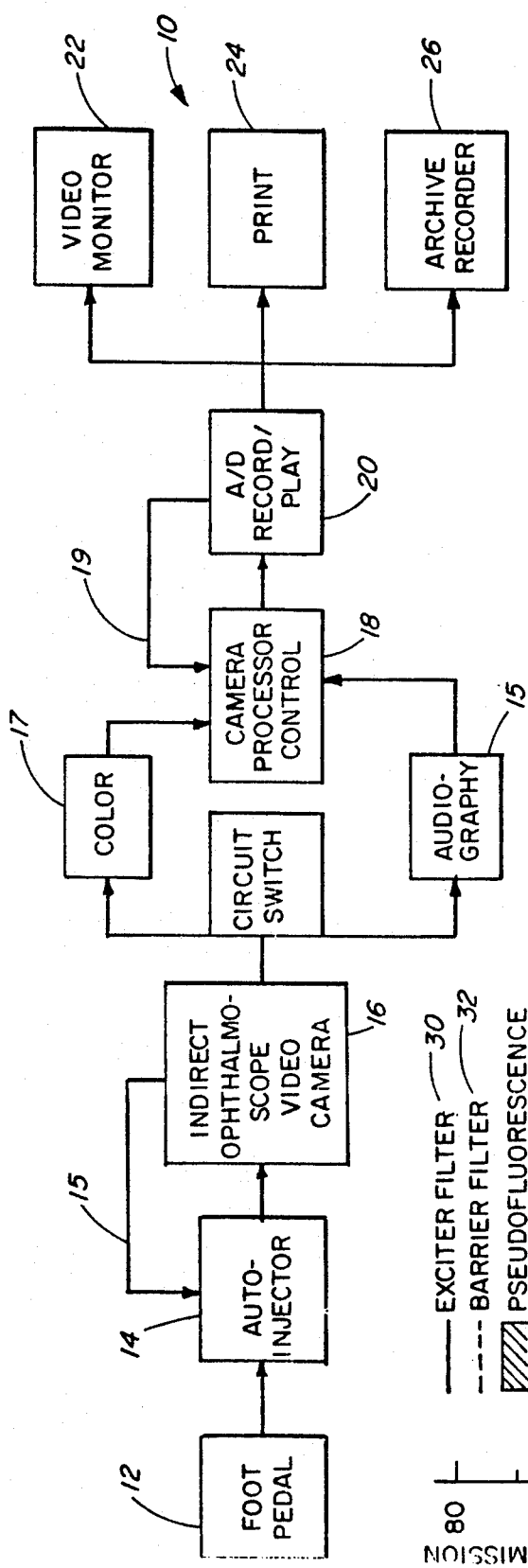
FIG. 1 is a diagrammatic representation of the retinal imaging system of the present invention.

Turning now to the accompanying Figures, and with particular reference to FIG. 1, there is shown the imaging system 10 in accordance with the present invention. Imaging system 10 consists generally of an foot pedal 12, an injector 13, an indirect ophthalmoscope or fundus camera 16, a camera process controller 18, and analog or digital recorder/player 20 and, optionally, a video monitor 22, printer 24 or archival recorder 26. The foot pedal 12 is activated by the practitioner to initiate the imaging process. Foot pedal 12 causes the injector 14, preferably an automatic injector, such as are known in the art, to initiate injection of a bolus of a fluorescent dye, such as sodium fluorescein or indocyanine green, into an intravenous line placed in the patient's arm. For purposes of illustration only, reference is made to the use of sodium fluorescein, and its spectral characteristics. Those skilled in the art will understand, however, that other fluorescent dyes suitable for human use are contemplated and may be used.

The indirect ophthalmoscope or fundus camera 16 is used to visualize the fluorescent retinal image in a conventional manner as well as imaged onto a video camera or cameras. The camera controller 18 receives the electronic video image of the fundus or ocular area and, when set for fluorescein or indocyanine green angiography, interposes electronic filters onto the energy to filter all but 520 nm wavelengths in the case of fluorescein or about 800 nm wavelengths in the case of indocyanine green. The electronic filter may consist of any opto-electronic coupling, such as a photo-sensor, which converts optical energy into electrical energy. The converted electric signals will correspond to the wavelength range of the optical signal. The correlation between wavelength and electronic frequency establishes the selection of appropriate electronic filter to filter out all but the frequency corresponding to the 520 nm light energy wavelength. Camera controller 18 may, for example, be a charge coupled device (CCD) camera of the type which receives optical energy and converts it to electronic signals for digital recording. The use of CCD cameras in digital image processing systems for analysis of coronary arteriograms and ventriculograms has been shown by Lowinger, T., et al., *Computers in Cardiology*, IEEE Computer Society, Los Alamitos, Calif. 1989, pp. 433-455, which is incorporated by reference. Additionally, the use of CCD sensors for image processing in analysis of electrophoresis gels, digital microscope imaging or in computer-assisted quantitative analysis of angiographic images recorded on 35 mm film is illustrated by Muser, M. H., et al., *Proceedings of SPIE—The International Society for Optical Engineering*, V. 1448, p. 106-112 (1991), which is also hereby incorporated by reference.

Alternative camera types which electronically record images in analog form may also be employed. An example of such analog recording is a video-tape recording of an eye fundus image taken from signal outputs to a monitor television as described by Sekine, A., et al., in U.S. Pat. No. 4,854,691. Sekine, hereby incorporated by reference, discloses a laser-based eye fundus camera system in which a photomultipliers are input with light reflected from the eye fundus and a photoelectric element is input with a part of a laser beam. The photomultipliers provide a signal, which is amplified and input to an analog/digital converter. The resulting digital signals are input to memory registers, which record the image frames, after the digital signals are output to a digital/analog converter to generate a video signal, for display on a monitor television. This type of analog/-digital to digital/analog conversion is not needed where CCD cameras are employed, but may be used in the present invention to provide analog signal processing.

Cameras which record and store images on microfloppy diskettes are known in the art and are available from Canon, Matushita or Sony. These types of cameras are capable of recording twenty-five high resolution or fifty lower resolution images in NTSC, high-definition format analog video images. Analog/digital recorder/-player 20 is preferably one of these types of analog camera recorders which receive the image from the indirect ophthalmoscope or fundus camera and record the image, in analog or digital form, on a microfloppy diskette, for later playback and record keeping. The camera 16 may be optically coupled to the indirect ophthalmoscope or fundus camera in any manner as is well known in the art.

The camera processor controller 18 may be used to modify images previously stored on the microfloppy diskette, or the images may be modified by a computer equipped with software for video frame grabbing and graphic manipulation.

Additionally, a video monitor 22 may be provided for viewing the image either directly from the camera controller 18 or as played from the analog digital recorder 20. A printer 24 may be provided to provide hard copy output of the stored images. Finally, an archival recorder 26, such as a compact disc based optical recorder such as CD-WORM may be used for archival record storage.

When used for color retinal photography, the camera controller 18 placed in its color setting 17 whereby all light spectra are transmitted to the camera recorder 20. However, when used for fluorescein or indocyanine green angiography, the camera controller is placed in its angiography setting 15 appropriate for the type of angiography being performed. The angiography setting 15 interposes the appropriate electronic filters on the signal transmitted from the camera controller 18, and passes only that signal corresponding to the fluorescence wavelength of the fluorescent dye employed.

Figure 4:
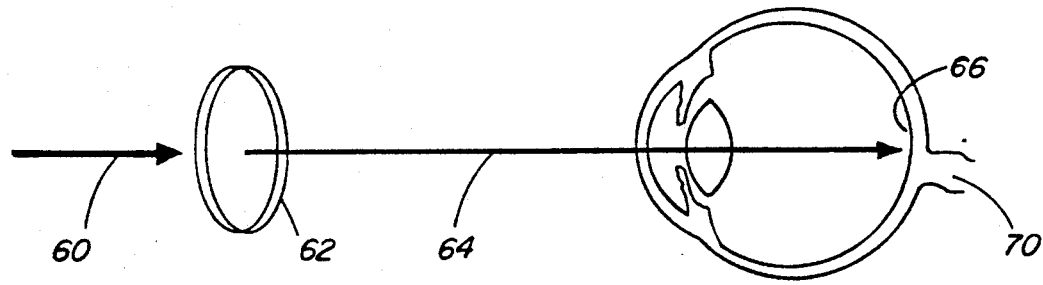
FIG. 4 is a diagrammatic illustration generally representative of the process of fluorescein angiography.
Figure 4:
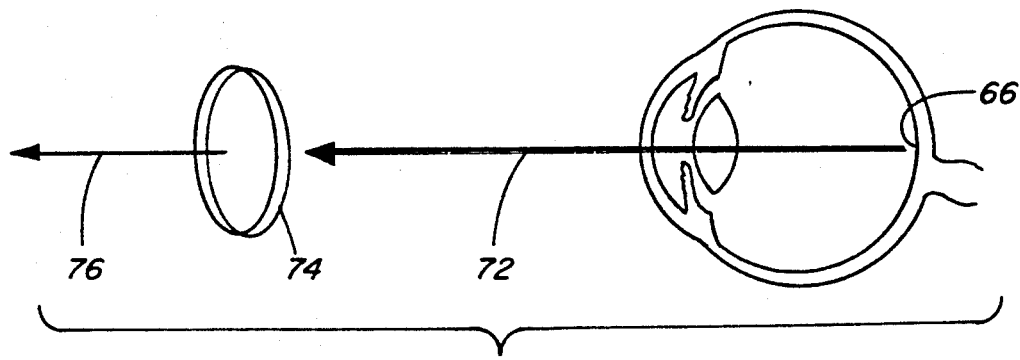

FIG. 4 is a diagrammatic representation of the process of fluorescein angiography. Light energy 60, such as that provided by a flash unit (not shown), is passed through the exciter filter 62. Exciter filter 62 is selected to pass a peak light wavelength corresponding to the excitatory energy required for the selected fluorescent dye, i.e., sodium fluorescein ~465 nm to 490 nm, the absorption peak of fluorescein excitation or for indocyanine green ~800 nm. The filtered light energy 64 is introduced into the eye and onto the eye fundus 66. The fundus vasculature is already perfused with the i.v. fluorescent dye 70. The fluorescent dye absorbs the excitatory light energy 64 and fluoresces at about 525 to 530 nm. The fluorescent energy, combined with reflected blue light form a returned light energy 72. A barrier filter 74 filters the returned light energy 72 to pass only the fluorescent energy at about 525 to 530 nm, and filter the reflected blue light at 465-490 nm. The filtered fluorescent energy 76 is passed through the barrier filter for viewing and/or recording.

Figure 2:
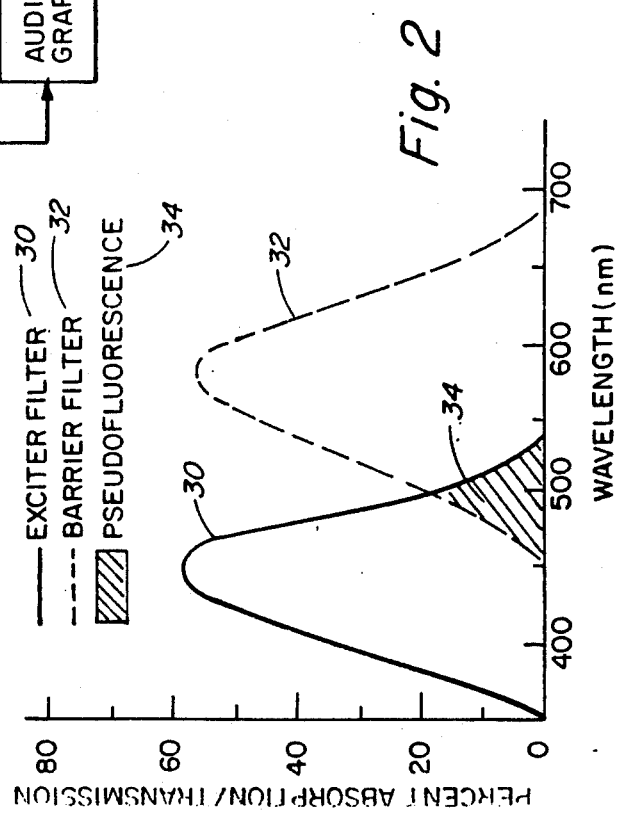
FIG. 2 is a graph of the spectral curves of exciter and barrier optical filters, illustrating the pseudofluorescence region.
Figure 3:
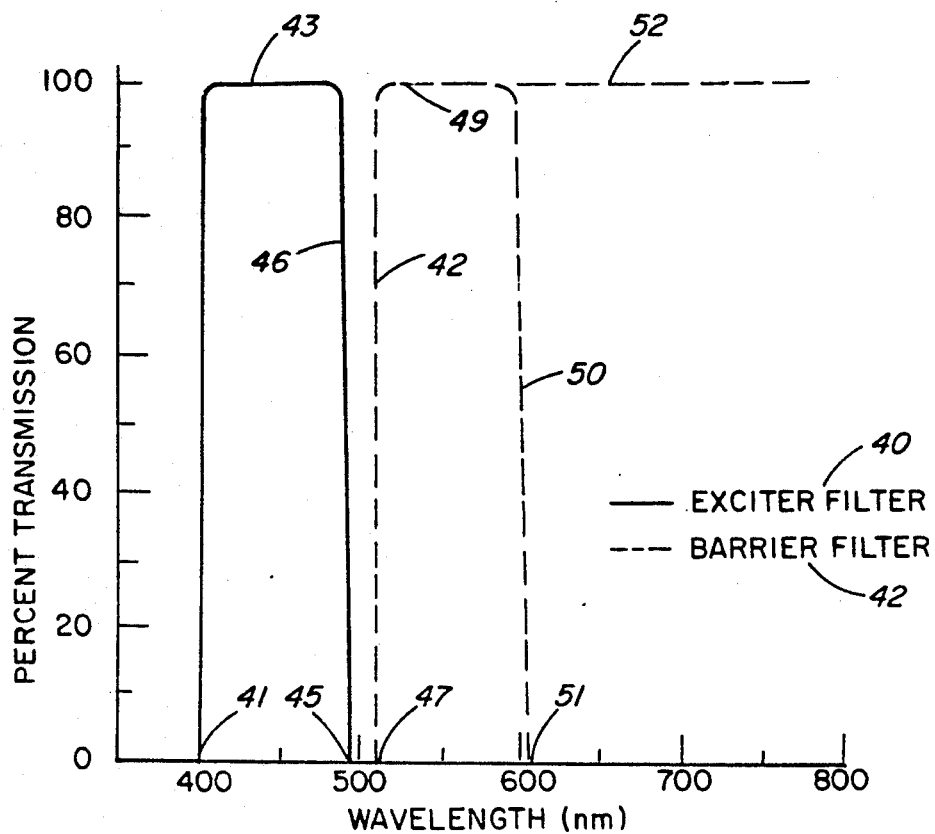
FIG. 3 is a graph illustrating the optimum spectral curves of exciter and barrier filters.

FIG. 2 is a graph depicting typical spectral curves for optical exciter 30 and barrier 32 filters. As noted above, the exciter filter 30 is typified by a slower absorption rate and a rapid decrease in light transmission. The barrier filter 32 is typified by a relatively faster absorption rate and a slower decrease in light transmission. FIG. 3, however, is illustrative of optimum or desired light transmission characteristics for exciter filters 40 or barrier filters 42. As illustrated in FIG. 3, the exciter filter 40 is preferably characterized by an immediate increase from 0% light transmission to 100% light transmission at the desired activation wavelength 41, or over a very narrow wavelength bandwidth, a plateau transmission 43 at the upper limit of filter transmission and an immediate decrease to 0% transmission once the upper or extinction wavelength 45 is reached. The barrier filter spectral curve 42 has similar characteristics, with a specific or narrow bandwidth activation wavelength 47 and a plateau 49. The barrier filter may be selected to have an immediate cessation of transmission 50 at an extinction wavelength 51 or may be configured for light transmission to a desired wavelength 52.

When set to the color mode 17, the system 10 of the present invention operates by activating a light source or flash unit on the indirect ophthalmoscope 16 to generate and image which is captured on the analog/digital recorder/player 20 for recording on a microfloppy diskette. The recorder/player 20 may be incorporated with or directly coupled to the indirect ophthalmoscope 16 to receive the retinal image. The retinal image stored on the microfloppy diskette may then be retrieved for playback and viewing on the television or video monitor 22, print out onto the printer 24 or archival storage on the archival recorder 26.

When set to the angiography mode 15, the system 10 of the invention operates in a like manner, except that an exciter filter is interposed in the flash unit or light source to provide the excitatory wavelength for the fluorescent dye employed. The exciter filter may be manually placed in the light path, or may be driven with a solenoid which permits strobing of the filtered excitatory light. Preferably the strobing should provide an excitatory flash at a rate of about one per second. The camera processor/controller 18 will receive both the reflected excitatory light and the fluorescence from the retina, and impose an electronic barrier filter, in a manner described above, to filter the reflected excitatory light and pass only the fluorescent spectrum. In the case of sodium fluorescein peak fluorescence occurs at 520 nm, hence, the electronic filter will pass electronic signals corresponding only to the 520 nm wavelength. In the case of indocyanine green peak fluorescence occurs at about 800 nm, hence, the electronic filter will pass electronic signals corresponding only to the 800 nm wavelength. The signals passed through the barrier filter will be stored on the microfloppy associated with the analog/digital recorder/player 20, for subsequent retrieval, playing, printing or archival storage as previously noted.

Thus, the present invention has been described with reference to its preferred embodiment. Those skilled in the art will understand, however, that changes in fluorescent dye selection, component parts, or processing parameters may be made within the scope of the present invention. The description of the preferred embodiment of the invention should not be construed as limiting the spirit and scope of the invention. For example, future developments in fluorescent dyes, fluorescent color spectra, and analog or digital color or monochrome processing may enhance the functionality of the present invention, without departing from the spirit and scope of the invention.

I claim:

1. An apparatus for visualizing, imaging and capturing ocular and retinal images, comprising:
   means for generating non-coherent light energy;
   portable means for directing generated light energy into an eye to be tested;
   filtering means for transmitting a desired wavelength of the generated light energy to the eye to be tested and passing a different desired wavelength of light energy emitted form the eye to be tested;
   signal processing means for receiving light energy emitted from the eye to be tested and converting the received light energy into at least one of an analog or digital electronic signal;
   recording means for receiving at least one of an analog or digital electronic signal, recording the received electronic signal onto an archival recording medium thereby obtaining a substantially complete recorded image of the eye fundus and generating an output signal; and
   viewing means for receiving the output signal received from the recording means and viewing the retinal image.

2. The apparatus according to claim 1, further comprising:
   means for injecting a fluorescent dye into the ocular or retinal vasculature and synchronizing the recording means;
   a fluorescent dye having known absorption and fluorescence wavelengths;
   an exciter filter which receives the generated light energy and passes only light energy corresponding to the absorption wavelength of the fluorescent dye; and
   a barrier filter which receives at least one of the light energies corresponding to the absorption wavelength of the fluorescent dye reflected from the eye to be tested and the fluorescence wavelength of the fluorescent dye, and passes only the fluorescence wavelength of the fluorescent dye.

3. The apparatus according to claim 1 wherein said filtering means further comprises an electronic circuit which transmits generated light energy having a wavelength substantially corresponding only to an absorption wavelength of a fluorescent dye injected into the eye to be tested, and passes only received light energy substantially corresponding to a fluorescent wavelength, of the fluorescent dye, emitted from the eye to be tested.

4. The apparatus according to claim 1, wherein said recording means further comprises an electronic camera which records optical light energy as at least one of analog or digital signals on a recording medium.

5. The apparatus according to claim 4, wherein said electronic camera further comprises an electronic camera electronically coupled to a recorder/reader for electromagnetically recording analog signals onto a magnetic medium.

6. The apparatus according to claim 1, wherein said viewing means further comprises at least one of an analog or digital video display.

7. An optical apparatus for combined indirect ophthalmoscopy and angiography of the eye fundus, comprising:
   a light generator for generating non-coherent light of a wavelength capable of generating fluorescence radiation from a fluorescent material circulating in blood vessels of an eye fundus of a person to be tested;
   a portable light director for aiming light into the fundus of the eye of a person to be tested;
   a light receiver for receiving light emitted from the eye fundus of a person to be tested;
   a photo-electric converter for converting light signals received by the light receiver to electrical signals;
   an electronic circuit switchable to pass all electrical signals, for indirect ophthalmoscopy, and to filter the electrical signals such that only electrical signals corresponding to the optical wavelength of the fluorescence pass through the electronic circuit, for angiography; and a recorder/player for recording the filtered electronic signals onto an archival recording medium and providing an output signal for viewing the recorded signals on a video display.

8. The optical apparatus according to claim 7, wherein said recorder/player further comprises an electronic camera which records optical light energy as at least one of analog or digital signals on a recording medium.

9. The optical apparatus according to claim 8, wherein said electronic camera further comprises an electronic camera electronically coupled to a recorder/reader for electromagnetically recording analog signals onto a magnetic medium.

10. The apparatus according to claim 7, wherein the video display further comprises at least one of an analog or digital video display.

11. A method of visualizing ocular and retinal anatomies, comprising the steps of:
 exposing an eye to be tested to a portable, non-coherent light source;
 receiving light emitted from the eye to be tested;
 converting said received light to electronic signals;
 processing said electronic signals by selecting one of a full spectrum of electronic signals corresponding to the full spectrum of received light or identified spectra of electronic signals corresponding to a identified wavelengths of received light;
 recording said processed electronic signals onto a recording medium; and
 viewing said processing electronic signals either directly or from said recording medium on a video display capable of generating an optical image from the electronic signals.

12. The method of claim 11, wherein said step of exposing the eye to be tested to a portable, non-coherent light source further comprises the step of generating fluorescence radiation from a fluorescent material circulating in a blood vessel of an eye fundus of a person to be tested.

13. The method of claim 12, wherein said step of processing the electronic signals further comprises the step of selecting electronic signals corresponding to a peak optical wavelength of the fluorescence radiation, and filtering non-selected electronic signals, thereby allowing said selected electronic signals to pass to said recorder.

14. The method claim 11, wherein said step of receiving light emitted from the eye to be tested further comprises the step of providing an electronic camera which records optical light energy as at least one of analog or digital signals on a recording medium.

* * * * *